United States Patent
Mendonca et al.

(10) Patent No.: US 9,324,155 B2
(45) Date of Patent: Apr. 26, 2016

(54) SYSTEMS AND METHODS FOR DETERMINING PARAMETERS FOR IMAGE ANALYSIS

(71) Applicant: General Electric Company, Schenectady, NY (US)

(72) Inventors: Paulo Ricardo Mendonca, Niskayuna, NY (US); Dirk Ryan Padfield, Niskayuna, NY (US); Chandan Kumar Mallappa Aladahalli, Bangalore (IN); Shubao Liu, Niskayuna, NY (US); Theresa Rose Broniak, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 123 days.

(21) Appl. No.: 14/202,853

(22) Filed: Mar. 10, 2014

(65) Prior Publication Data

US 2015/0254866 A1    Sep. 10, 2015

(51) Int. Cl.
*G06K 9/00* (2006.01)
*G06T 7/00* (2006.01)

(52) U.S. Cl.
CPC ............... *G06T 7/0081* (2013.01); *G06T 7/004* (2013.01); *G06T 2207/10136* (2013.01); *G06T 2207/20081* (2013.01); *G06T 2207/30101* (2013.01)

(58) Field of Classification Search
USPC .................................................. 382/128–134
See application file for complete search history.

(56) References Cited

U.S. PATENT DOCUMENTS

| | | | |
|---|---|---|---|
| 5,182,776 A | 1/1993 | Suzuki et al. | |
| 6,664,973 B1 | 12/2003 | Iwamoto et al. | |
| 7,065,243 B2 | 6/2006 | Boland et al. | |
| 7,796,815 B2 | 9/2010 | Muschler et al. | |
| 8,036,481 B2 | 10/2011 | Sakurai et al. | |
| 8,055,034 B2 | 11/2011 | Dube et al. | |
| 8,121,383 B2 | 2/2012 | Sipe et al. | |
| 8,355,554 B2 | 1/2013 | Ma et al. | |
| 8,391,603 B2 | 3/2013 | Tizhoosh et al. | |
| 2001/0016057 A1* | 8/2001 | Eck | H04N 5/3653 382/132 |
| 2003/0007598 A1* | 1/2003 | Wang | A61B 6/463 378/37 |

(Continued)

OTHER PUBLICATIONS

Cao et al., "Association of Carotid Artery Intima-Media Thickness, Plaques, and C-Reactive Protein with Future Cardiovascular Disease and All-Cause Mortality: The Cardiovascular Health Study", Circulation, pp. 32-38, vol. 116, Issue 1, Jul. 3, 2007.

(Continued)

*Primary Examiner* — Alex Liew
(74) *Attorney, Agent, or Firm* — Seema S. Katragadda (57) ABSTRACT

Systems and methods for determining parameters for image analysis are provided. One method includes obtaining ultrasound data of an object, generating an image of the object, and identifying a region of interest in the image. The method also includes determining a plurality of spatially varying parameters for image analysis of the region of interest using prior information for one or more objects of interest, including prior location information for the one or more objects of interest, and wherein the plurality of spatially varying parameters are determined for a plurality of sections of the region of interest and different for at least some of the plurality of sections. The method further includes using the plurality of spatially varying parameters for performing image analysis of the region of interest in the image to determine the location of the one or more objects of interest.

17 Claims, 7 Drawing Sheets

(56) References Cited

U.S. PATENT DOCUMENTS

| | | | |
|---|---|---|---|
| 2005/0074154 A1* | 4/2005 | Georgescu | G06T 7/20 382/128 |
| 2005/0129296 A1* | 6/2005 | Setala | G06T 7/0046 382/131 |
| 2006/0245640 A1 | 11/2006 | Szczuka | |
| 2007/0053563 A1* | 3/2007 | Tu | G06K 9/6256 382/128 |
| 2007/0255139 A1* | 11/2007 | Deschinger | A61B 8/14 600/443 |
| 2007/0263915 A1* | 11/2007 | Mashiach | G06K 9/342 382/130 |
| 2008/0170770 A1* | 7/2008 | Suri | A61B 8/12 382/128 |

OTHER PUBLICATIONS

Javier et al., "Imaging of Atherosclerotic Cardiovascular Disease", Nature 451, pp. 953-957, Feb. 21, 2008.

Chiu et al., "Three-Dimensional Carotid Ultrasound Segmentation Variability Dependence on Signal Difference and Boundary Orientation", Ultrasound Med Biol, pp. 95-110, vol. 36, Issue 1, Jan. 2010.

Muntendam et al., "The BioImage Study: Novel Approaches to risk Assessment in the Primary Prevention of Atherosclerotic Cardiovascular Disease—Study Design and Objectives", Am Heart J, pp. 49-57, vol. 160, Issue 1, Jul. 2010.

"Carotid Artery Disease", Vascular & Endovascular Surgery, 2012.

Weisstein, "Circle-Circle Intersection", Wolfram MathWorld.

\* cited by examiner

SYSTEMS AND METHODS FOR DETERMINING PARAMETERS FOR IMAGE ANALYSIS

BACKGROUND

Image analysis algorithms for detection, segmentation, characterization and other forms of information extraction from image data typically rely on the adjustment of specific algorithm parameters, such as threshold levels, noise levels, or the expected size of depicted structures when performing the analysis. For example, for image segmentation, different parameters are set to facilitate identifying regions of interest for use in medical image analysis. In particular, image segmentation may be used to segment structures from background, which may be performed as part of the image analysis, such as for visualization, quantitative image analysis, and image guided intervention.

Image analysis, including image segmentation can be difficult to perform because of the large variability of shape and appearance of different structures. Conventional algorithms that perform image analysis may initially perform image segmentation. However, when image analysis algorithms use rigid models or spatially fixed parameters for performing the image analysis, the results may be inaccurate. For example, ultrasound systems are increasingly used to detect carotid plaque, which may be used to predict cardiovascular disease. Because of the rigid nature of conventional image analysis algorithms and the parameters used, the carotid plaque may not be properly identified, resulting in improper diagnosis or requiring additional scans.

BRIEF DESCRIPTION

In one embodiment, a method for setting parameters for image analysis of ultrasound images is provided. The method includes obtaining ultrasound data of an object, generating an image of the object, and identifying a region of interest in the image. The method also includes determining a plurality of spatially varying parameters for image analysis of the region of interest using prior information for one or more objects of interest, including prior location information for the one or more objects of interest, and wherein the plurality of spatially varying parameters are determined for a plurality of sections of the region of interest and different for at least some of the plurality of sections. The method further includes using the plurality of spatially varying parameters for performing image analysis of the region of interest in the image to determine the location of the one or more objects of interest.

In another embodiment, a method for setting parameters for image analysis of ultrasound images is provided. The method includes obtaining ultrasound data of an object, generating an image of the object, and identifying a region of interest in the image. The method also includes determining a plurality of spatially varying parameters for image analysis of the region of interest using prior information for one or more objects of interest, wherein the prior information defines a relative prior frequency of an occurrence of the one or more objects of interest in one or more different locations within a region of interest. The method further includes using the plurality of spatially varying parameters for performing image analysis of the region of interest in the image to determine the location of the one or more objects of interest.

In another embodiment, an ultrasound system is provided that includes a probe configured to acquire ultrasound data, a processor configured to generate image data, and a parameter setting system that determines a plurality of spatially varying parameters for image analysis of a region of interest in the image data using prior information for one or more objects of interest, including prior location information for the one or more objects of interest. The plurality of spatially varying parameters is determined for a plurality of sections of the region of interest and different for at least some of the plurality of sections. The ultrasound system also includes an image analysis system that uses the plurality of spatially varying parameters for performing image analysis of the region of interest to determine a location of the one or more objects of interest.

DETAILED DESCRIPTION

The following detailed description of certain embodiments will be better understood when read in conjunction with the appended drawings. It should be understood that the various embodiments are not limited to the arrangements and instrumentality shown in the drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules, systems, or units shown in the attached figures may represent the hardware that operates based on software or hardwired instructions, the software that directs hardware to perform the operations, or a combination thereof.

Described herein are methods and systems for determining parameters for performing image analysis, which may include, for example, detection, segmentation, characterization, and other forms of information extraction from image data. In various embodiments, spatially varying parameters for image analysis algorithms are set or defined using prior information, (e.g., relative frequency of detection of an object of interest in a region of interest). It should be noted that prior information may be any type of information, for example, with respect to a particular subject or particular group, and may be referred to herein as priors.

In some embodiments, the use of priors changes the setting of relevant parameters of an algorithm in accordance with the specific image region under analysis, and uses variable settings for different image regions. The prior knowledge may be acquired, for example, through the analysis of a training dataset, which contains exemplars of structures of objects of interest within the image, or through the application of physical models that describe the image formation process.

In general, as used herein, a prior is a mapping $x \rightarrow k(x)$ from a given region x of the image into a possibly multidimensional parameter k in a predefined parameter space. Accordingly, when the region x of the image is under analysis, the prior(s) provides the appropriate value $k(x)$ that parameters relevant to the analysis algorithm assume or use. It should be noted that there may not be any alignment between regions in the image and in the prior. In this case, a mapping T: $X \rightarrow Y$ is applied to the image region x, resulting in a new region $y=T(x)$, which is the region corresponding to x in the coordinate system of the prior k. In this situation, an algorithm operating on image region x has corresponding relevant parameters set to a value given by $k(T(x))$, determined jointly by the prior k and the mapping T.

Examples of k include a function that establishes the likelihood $k(x)$ of observing a structure or object of interest at location x, in which case $k(x)$ may be used as a threshold for identifying one or more objects (e.g., deciding for or against the presence of the structure or object of interest) at location x. Another example is a function that prescribes the expected value of the standard deviation $k(x)$ of random noise affecting region x, in which case $k(x)$ may be used as the spatially varying standard deviation in a specific probability model for the random noise in the image. It should be noted that the mapping T, when the images and the prior have different coordinate systems, can be obtained through one or more methods of image registration methods, such as known in the art.

Figure 1:
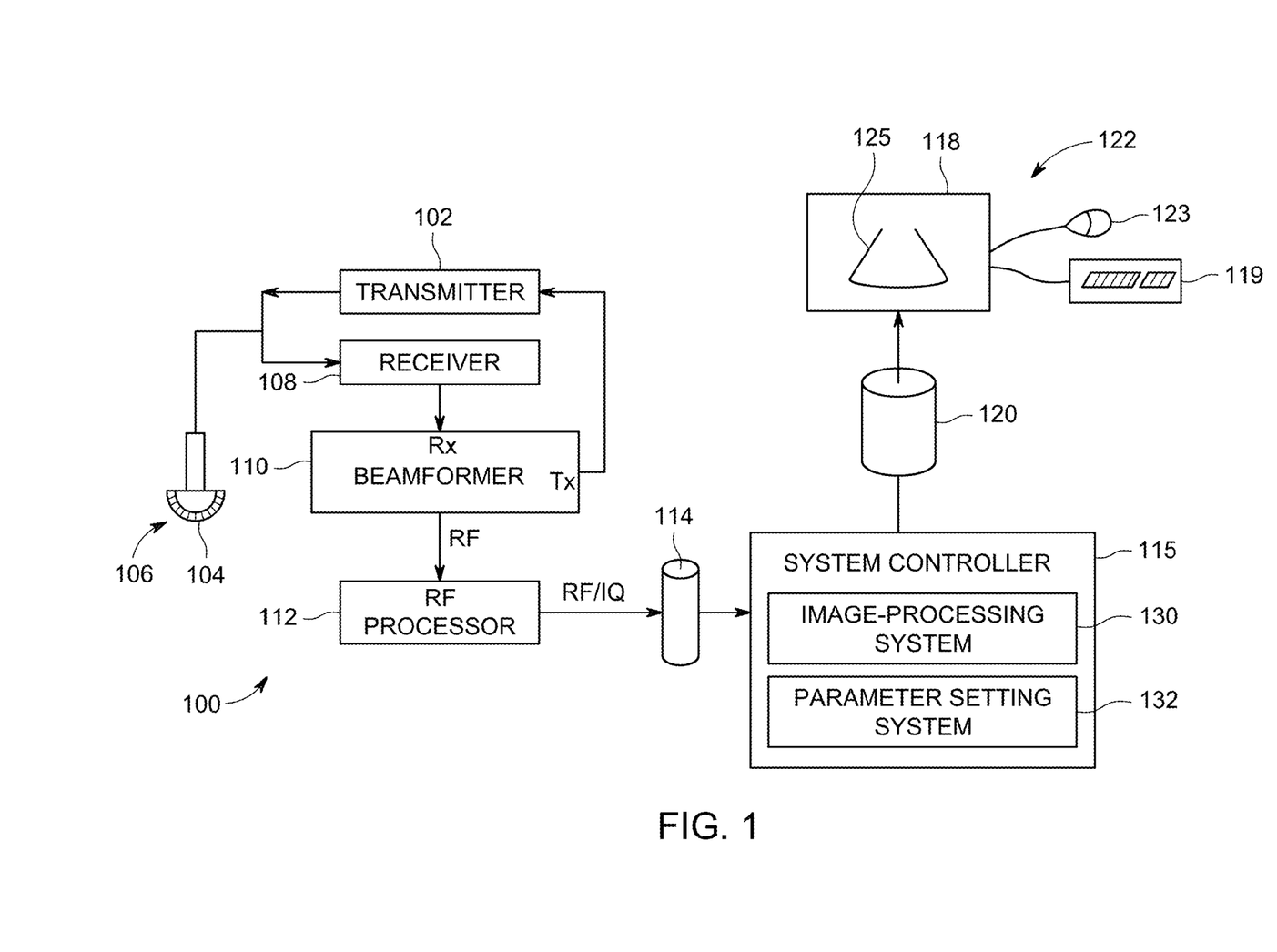
FIG. 1 is a block diagram of an ultrasound system in accordance with an embodiment.

FIG. 1 illustrates a block diagram of a system 100 according to one embodiment. In the illustrated embodiment, the system 100 is an imaging system and, more specifically, an ultrasound imaging system. However, it should be understood that embodiments set forth herein may be implemented in combination other types of medical imaging modalities (e.g., MR, CT, PET/CT, etc.). Furthermore, it should be understood that other embodiments do not actively acquire medical images. Instead, embodiments may retrieve or obtain image data that was previously acquired by an imaging system and analyze the image data as described in more detail herein.

As shown, the system 100 includes multiple components. The components may be coupled to one another to form a single structure, may be separate, but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels, be transported on a cart or may be a handheld or hand-carried device.

In the illustrated embodiment, the system 100 includes a transmitter 102 that drives an array of elements 104, for example, piezoelectric crystals, within a diagnostic ultrasound probe 106 (or transducer) to emit pulsed ultrasonic signals into a body or volume (not shown) of a subject. The elements 104 and the probe 106 may have a variety of geometries. The ultrasonic signals are back-scattered from structures in the body, for example, blood vessels and surrounding tissue, to produce echoes that return to the elements 104. The echoes are received by a receiver 108. The received echoes are provided to a beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

The system 100 also includes a system controller 115 that includes a plurality of systems, which may, for example, be part of a single processing unit (e.g., processor) or distributed across multiple processing units. The system controller 115 is configured to control operation of the system 100, as well as perform post-acquisition processing, such as using one or more different image analysis algorithms. For example, the system controller 115 may include an image-processing system 130 (which may be embodied as or include an image analysis system) that receives image data (e.g., ultrasound signals in the form of RF signal data or IQ data pairs) and processes image data. For example, the image-processing system 130 may process the ultrasound signals to generate slices or frames of ultrasound information (e.g., ultrasound images) for displaying to the operator. The image-processing system 130 may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D).

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like.

In operation, an ultrasound system may acquire data, for example, volumetric data sets by various techniques (for example, 3D scanning, real-time 3D imaging, volume scanning, 2D scanning with transducers having positioning sensors, freehand scanning using a voxel correlation technique, scanning using 2D or matrix array transducers, and the like). Ultrasound images 125 may be displayed to the operator or user on a display device 118, which may include identified regions of interest (e.g., plaque) as described in more detail herein.

The system controller 115 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes the display device 118. In some embodiments, the user interface 122 may also include one or more input devices, such as a physical keyboard 119, mouse 123, and/or touchpad. In one embodiment, the display device 118 is a touch-sensitive display (e.g., touchscreen) that can detect a presence of a touch from the operator and can also identify a location of the touch. The touch may be applied by, for example, at least one of an individual's hand, glove, stylus, or the like. As such, the touch-sensitive display may also be characterized as an input device that is configured to receive inputs from the operator. The display device 118 also communicates information to the operator by displaying the information to the operator. The display device 118 and/or the user interface 122 may also communicative audibly. The display device 118 is configured to present information to the operator during the imaging session. The information presented may include ultrasound images, graphical elements, user-selectable elements, and other information (e.g., administrative information, personal information of the patient, and the like).

In addition to the image-processing system 130, the system controller 115 may also include a parameter setting system 132 that sets one or more parameters to be used by the system controller, such as for image analysis. For example, as described in more detail herein, the parameter setting system 132 may be configured to set spatially varying parameters for image analysis through the use of prior information. As one particular non-limiting example, for a plaque determination application, the parameter setting system 132 uses initial priors on the angular distribution of plaques, with the priors used to control the thresholds for plaque detection at different angles of the carotid wall.

Figure 2:
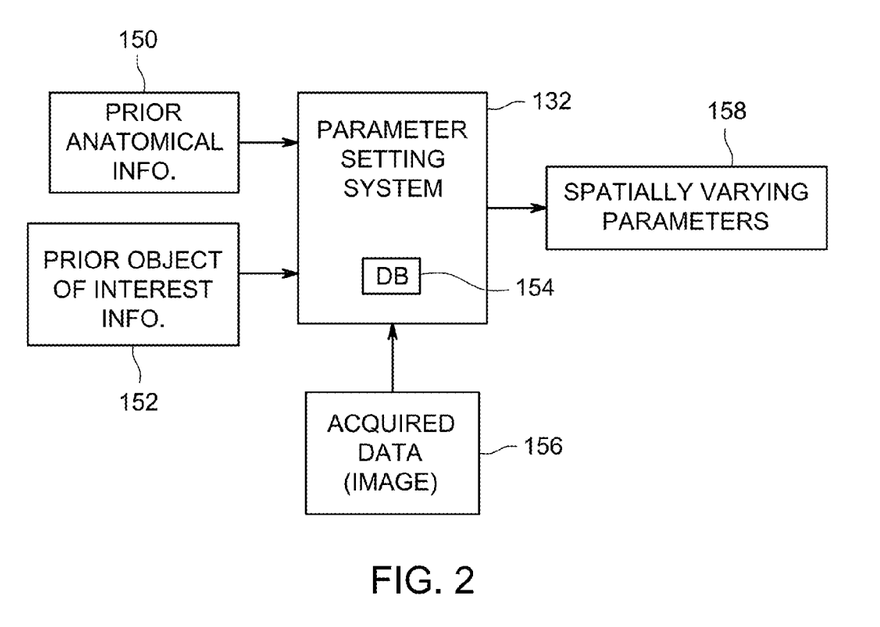
FIG. 2 is a block diagram of a parameter setting system in accordance with an embodiment.

FIG. 2 generally illustrates the inputs that may be received and used by the parameter setting system 132 and the outputs generated. In particular, the parameter setting system 132 receives as input data different types of prior information. For example, in the illustrated embodiment, the parameter setting system 132 receives prior anatomical information 150 and/or prior object of interest information 152. In some embodiments, the information may be combined, such as including the relative frequency of an object of interest (e.g., plaque) in a region of interest (e.g., a portion of the carotid artery). Thus, different relative frequencies and thresholds may be set based on prior information relating to the frequency that plaque (or other objects of interest) are present or found in a particular area or regions of interest. In some embodiments, the prior information 150 and 152 includes data relating to the frequency at which objects of interest are present in the region of interest, as well as the false positives that are detected. Thus, for example, in a plaque detection application, the parameter setting system 132 uses prior information to determine the likelihood of an object being plaque in a particular region and setting spatially varying parameters accordingly. It should be noted that the determination of the likelihood of a detected object being an object of interest may be applied at the pixel (or voxel) level or on a portion of the image, such as region of interest, that may be extracted or segmented from the overall image.

In some embodiments, a database 154 is provided, which is accessed by the parameter setting system 132 and the information stored therein used to determine how to set or vary different parameters. The database 154 may include, for example, an atlas that provides one or more different values for a parameter to be used as part of the image analysis, which is specific to a particular region of interest, such as a particular portion of anatomy. In various embodiments, acquired data 156, which may be currently acquired or previously acquired also is used by the parameter setting system 132 to set one or more of the parameters. For example, the acquired image data may be used to perform a registration of an image to an atlas. In the example of the carotid artery, an initial determination may be made as to the location of the bifurcation of the carotid artery before image analysis is performed. Thus, in various embodiments, one or more parameters for an image analysis may be varied based on the physical location of interest. For example, lung nodules are more common at the top of the lungs, and as such, a spatially varying parameter may be changed to set a value (e.g., decrease a threshold value) that indicates a higher likelihood of detecting a nodule at a top of the lungs.

In operation, using the prior information 150 and 152, the parameter setting system 132 may access the database 154, and also use the acquired data 156 to set one or more spatially varying parameters 158. The spatially varying parameters 158 may be set for different portions of the image analysis process. For example, the spatially varying parameters 158 may be adjusted to define different threshold outputs for an image analysis algorithm. As another example, the spatially varying parameters 158 may be adjusted to determine the manner in which a particular value is set for performing part of the image analysis, such as for an initial segmentation. Thus, the parameter setting system 132 may determine or set spatially varying parameters 158 at the front end of the image analysis process and/or at the back end of the image analysis process.

Figure 3:
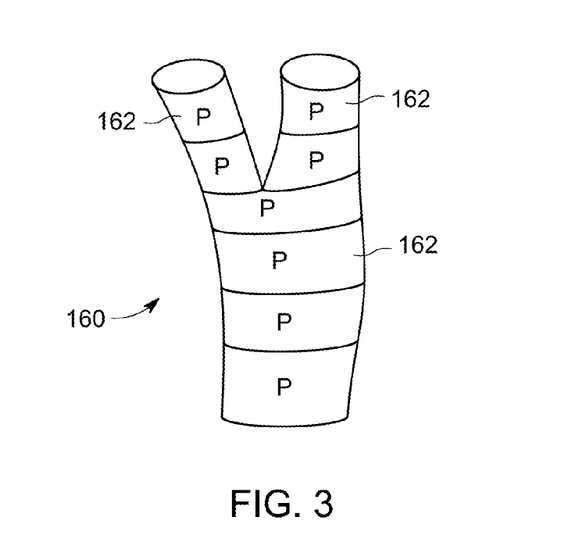
FIG. 3 is a diagram illustrating an atlas in accordance with an embodiment.

FIG. 3 illustrates an example of an atlas 160 in accordance with an embodiment that may be used to adjust or set the spatially varying parameters 158. In this embodiment, the atlas 160 is a portion of the carotid artery, which is divided into a plurality of different sections 162. The sections 162 generally define different physical regions of the carotid artery. It should be noted that the size, shape, and/or number of sections 162 may be varied as desired or needed. Accordingly, more or less sections 162 may be defined and the sections may be divided in different directions (e.g., vertical instead of or in addition to horizontal as shown in FIG. 3). In accordance with various embodiments, each section 162 defines a set of spatially varying parameters P to be used for one or more image analysis algorithms. Thus, the atlas 160 may be accessed to determine the spatially varying parameters for image analysis that is performed using a determined image analysis process or multiple image analysis processes. It should be noted that the spatially varying parameters P for each of the sections 162 may be different, may be the same, or may be partially the same (e.g., some overlapping values). For example, one or more parameters may be similarly or differently set based on the spatially varying parameters P in each of the sections 162. In some embodiments, a threshold value for one or more parameters is defined in each of the sections 162 based on prior information, such as the prior information 150 and 152 (shown in FIG. 2). Thus, spatial parameters may be varied to facilitate or improve the likelihood of an image analysis algorithm identifying an object of interest.

Figure 4:
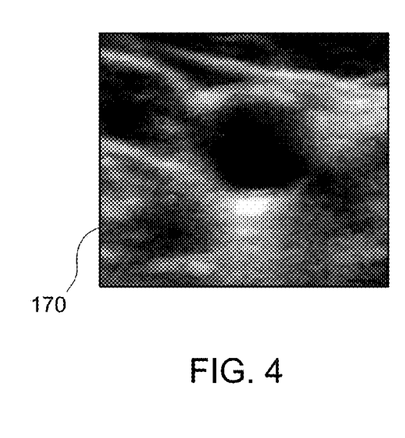
FIG. 4 is an image of a carotid artery that may be image processed in accordance with various embodiments.
Figure 5:
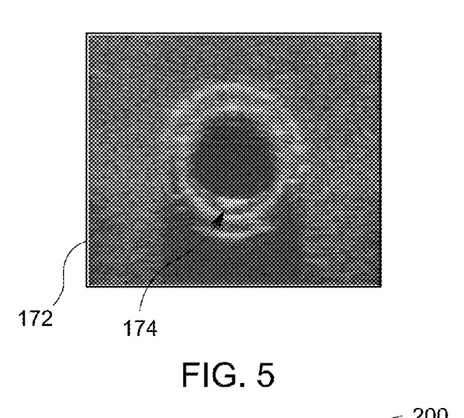
FIG. 5 is an image of an object of interest that may be identified in accordance with various embodiments.

For example, FIG. 4 is an image 170 of a carotid artery. The image data for generating the image 170 and the generation of the image 170 may be performed by the system 100 (shown in FIG. 1). In various embodiments, spatially varying parameters are determined and used in accordance with various embodiments for performing image analysis on the image 170. For example, the atlas 160 (shown in FIG. 3) may be used to apply the spatially varying parameters when processing different regions of the image 170. As a result of using one or more embodiments, improved identification of objects of interest may be provided. For example, FIG. 5 is an image 172 showing a portion of the carotid artery. The image 172 may be analyzed with one or more image analysis algorithms to identify object of interest. In the illustrated image 172, using spatially varying parameters in accordance with various embodiments allows for improved visualization or increased likelihood of the image analysis identifying (in this example) vulnerable plaque 174. For example, in various embodiments, the vulnerable plaque 174 may be automatically identified (and, for example, highlighted or circled) using image analysis programs that perform image analysis using spatially varying parameters as described in more detail herein.

Accordingly, spatially varying parameters may be determined for use in different types of image analysis, such as for different types of image segmentation, image-based detection, and image-based quantification. For example, spatially varying parameters determined in accordance with various embodiments may be used with segmentation algorithms such as thresholding, clustering methods, edge detection algorithms, region-growing methods, split-and-merge methods, partial differential equations-based methods, parametric methods, level set methods, graph partitioning methods, watershed methods, and/or multi-scale segmentation methods, among others. As other examples, spatially varying parameters determined in accordance with various embodiments may be used with image-based detection methods, such as template matching, histogram of oriented gradients, deformable parts models, Bayesian or statistical detection methods, and/or novelty detection methods, among others. As other examples, spatially varying parameters determined in accordance with various embodiments may be used with image-based quantification methods, such as wavelet-based texture analysis, intensity thresholding, methods based on Minkowski functionals, histogram-based methods, model-based quantification methods, and/or texture analysis by synthesis methods, among others.

By practicing one or more embodiments, varying parameters for image analysis algorithms are used based on where in the image the algorithms operates and with the guidance of pre-established domain knowledge relevant to the desired output of the particular image analysis algorithm in use. In various embodiments, the prior information can include, for example, information or knowledge of the factors that influence algorithmic performance on certain image regions. Use of such knowledge in image analysis algorithms in accordance with one or more embodiments can improve the performance of the image analysis.

For example, in various embodiments, application of spatial clinical information contained in large sets of images may be used to determine similar information in newer sets of images. Additionally, various embodiments can spatially guide and/or adapt image processing algorithms using spatial information in pre-existing images from different geographies, ethnicities, anatomical features, etc. enabling targeted analysis and outputs. Further, anatomical distribution of clinical data may be accurately captured and mining of imaging biomarkers and visualization can be enabled.

Figure 6:
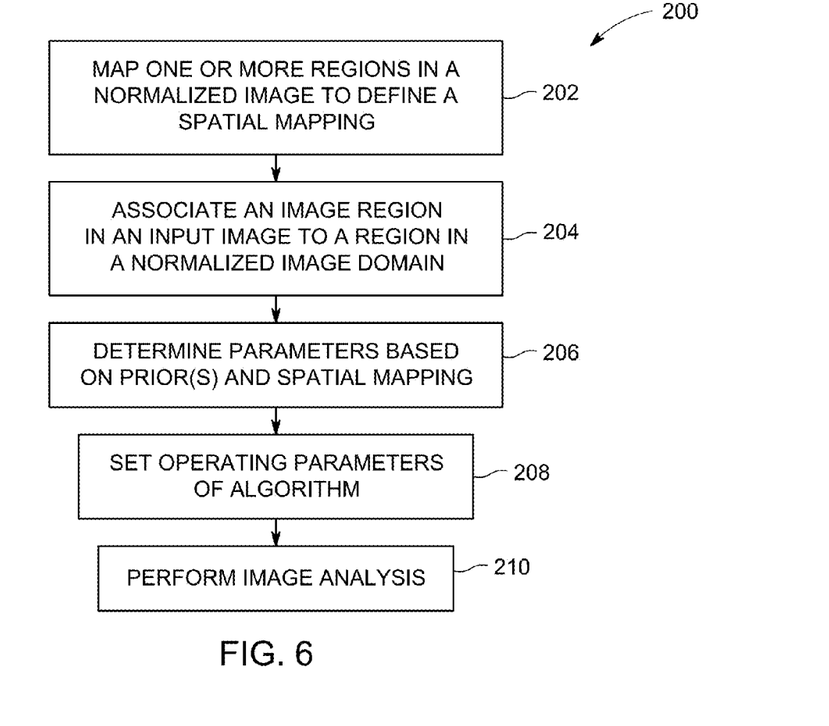
FIG. 6 is a flowchart of method in accordance with various embodiments.

A method 200 for setting spatially varying parameters and performing image analysis is shown in FIG. 6. In various embodiments, the method 200, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be able to be used as one or more algorithms to direct hardware to perform operations described herein.

The method 200 includes mapping one or more regions in a normalized image to define a spatial mapping at 202. For example, in various embodiments, a function k(y) is established or defined that maps regions y in a normalized image domain Y to a scalar or vector value k(y) of parameter(s) relevant to an image analysis algorithm A. Thereafter, an image region in an input image is associated to a region in a normalized image domain at 204. For example, once an image I is provided as input into algorithm A for analysis, the spatial mapping T: X→Y associates an image region x in the input image I to a region y=T(x) in the normalized image domain Y. It should be noted that if the input image I and the function k operate on regions already in the same coordinate system (e.g., already registered), the mapping T is not performed, or in some embodiments, defaults to the identity function.

The method 200 also includes at 206 determining parameters (namely spatially varying parameters) based on one or more prior(s) and the spatial mapping, and operating parameters for the algorithm A are set at 208. For example, when operating on region x, the algorithm A sets operating or processing parameters according to the value k(T(x)) jointly determined by the function k (the prior), and T (the spatial mapping). Using the parameters, an image analysis is performed at 210.

It should be noted that as the operating region x changes to an operating region x', the value(s) of the relevant parameter(s) k will also change, now given by k(T(x')). In various embodiments, the establishment of the particular function k is performed as an off-line process, i.e., before the application of algorithm A to the input image I, through the analysis of a training set or through manual intervention. However, results of the application of algorithm A to image I can be fed back into the function k, which is updated with information or knowledge acquired through the analysis. This update can be performed, for example, in a batch mode, such as by adding image I to the training set that was used to establish k and then re-determining k with the aid of the augmented dataset, or by manually intervening on the function k in the light of the results of applying A to image I.

Figure 7:
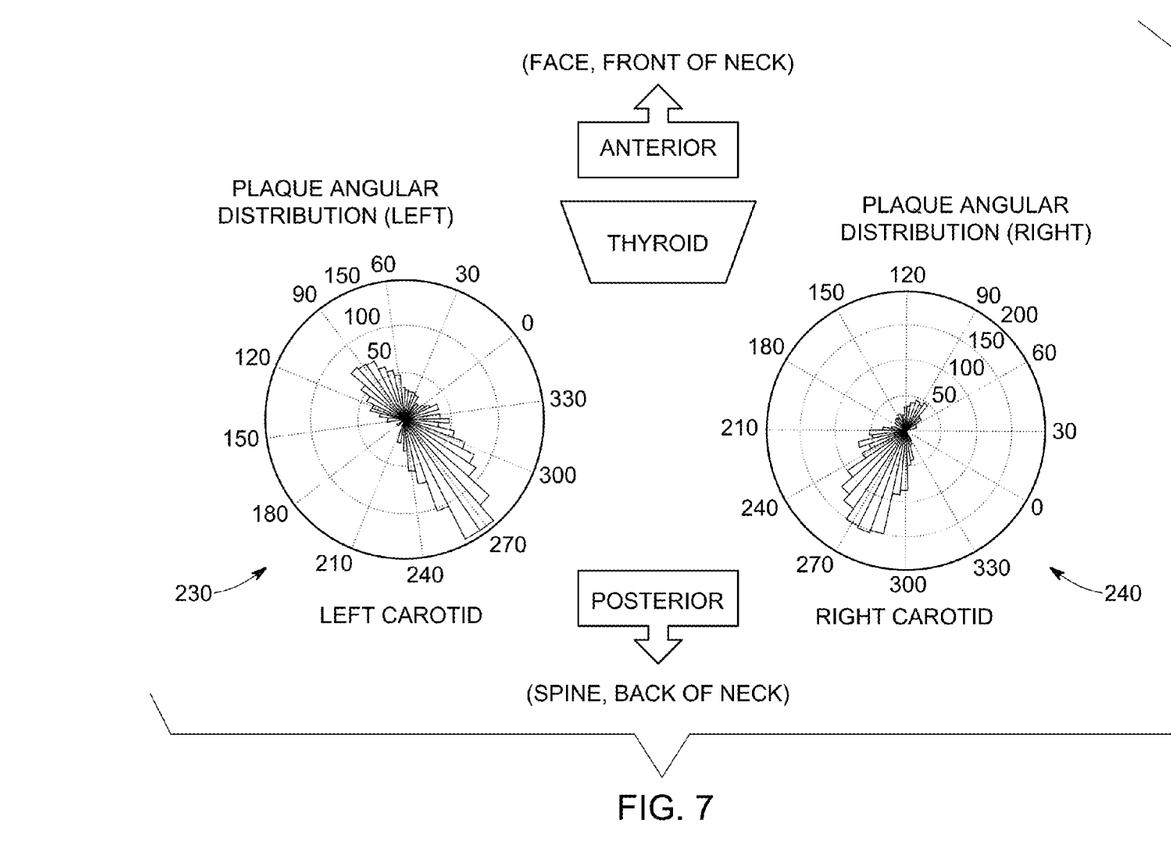
FIG. 7 are graphs illustrating priors based on the angular distribution of plaques that may be used in accordance with various embodiments.

For example, the polar graphs 230 and 232 shown in FIG. 7 illustrate priors based on the angular distribution of plaques, with the priors used to control the thresholds for plaque detection at different angles of the carotid wall. In particular, the polar graph 230 illustrates prior information for a plaque angular distribution of the left carotid and the polar graph 240 illustrates prior information for a plaque angular distribution of the right carotid. It should be noted that the polar graphs 230 and 232 are oriented with respect to the anterior and posterior of the thyroid as illustrated by the arrows in FIG. 7. The angular distribution of plaque may be determined based on, for example, a plurality of detected plaques in images of previous carotid arteries. The angular distribution may be used to determine a likelihood of plaque detection at different angular distributions to define spatially varying parameters as described in more detail herein.

Variations and modifications are contemplated. For example, updating or establishing k may be performed through the pooling of data or expert opinions distributed over different geographical locations. This pooling can be achieved, for example, through online/offline collaboration tools and/or data hosted in cloud computing systems.

Determination of spatially varying parameters in accordance with the embodiments described herein was performed to determine the normalized image domain of the canonical carotid. In particular, the bifurcation points of greater than 4000 carotid circle stacks were used to co-register the images. The canonical carotid was then computed as the average of the registered carotid circle stacks. The spatial mapping T was then determined using the co-registration, which was used to determine a 3D transformation matrix from a given carotid to the canonical carotid. The function k(x) was then determined, which is the likelihood of a plaque being present at the region x of the carotid artery. In this example, k(x) was computed by utilizing the plaque locations on greater than 2000 images with plaque locations and size marked by clinicians. The spatial mapping T from an image to the canonical carotid was computed for each of the images as described above, which was then used to transfer the location and size of the plaques to the canonical carotid. The function k(x) was then computed as a size weighted summation of plaque location centered kernels (a Gaussian in this embodiment) with a spread in R, Theta and Z proportional to the size of the plaque. In this example, varying parameters for image analysis algorithms were determined according to where in the image the algorithm operates and with the guidance of prior information. The various embodiments the may be able to detect one or more objects of interest, such as shown in FIG. 5.

In various embodiments, spatially varying parameters may be applied to threshold an output of the image analysis algorithm. In this embodiment, the output threshold is changed (e.g., varying the threshold to determine the likelihood of an object of interest), such that the internal parameters of the image analysis algorithm are not changed. In some embodiments, the spatially varying parameters are changed to determine the operation of initially identifying regions of interest by changing the internal parameters of the image analysis algorithm. For example, if the image analysis algorithm is in an area where plaque is known to be of a larger or more detectable size, increased image smoothing may be performed to allow easier viewing and identification of the plaque (while not smoothing out the plaque, which may occur if the plaque is smaller in size). Thus, prior knowledge or information of the particular area and known characterization of that area may be used to adjust the spatially varying parameters. It should be noted that the output determination for the image analysis algorithm additionally may be changed in combination with changing the internal parameters of the image analysis algorithm. For example, the image may be smoothed, but the output threshold set based on prior knowledge that a detection of the object is not expected. For example, using prior knowledge of the average size of carotid plaque (e.g., 5 mm), but with knowledge that the carotid plaque is larger in particular physical locations, the spatially varying parameters may be varied based on the expected size and location of the carotid plaque. Thus, the various embodiments may facilitate, for example, segmentation.

Other embodiments are contemplated, for example using spatially varying parameters as described herein, such as using a quantification method that may be focused in a particular area, for example, for an emphysema study, where analysis may be performed to identify areas of severity, but that only present in very specific regions. The spatially varying parameter may be adjusted based on these areas.

Thus, various embodiments provide spatially varying parameters for image analysis that use prior information. For example, image analysis parameters may be varied based on one or more locations in an image where a particular algorithm operates and with the use of prior domain knowledge or information relevant to the particular analysis algorithm.

It should be noted that the various embodiments may be used in combination with or to perform different types of image analysis. For example, using the spatially varying priors of one or more embodiments, image segmentation may be performed to partition an image to locate objects or boundaries in the image. Once identified, the objects or boundaries may be automatically labeled, for example, the pixels in the image may be labeled such that pixels with the same label have certain similar characteristics. Thus, with a stack of images, using image segmentation and spatially varying parameters as described herein, 3D image reconstruction, for example, may be performed.

Figure 8:
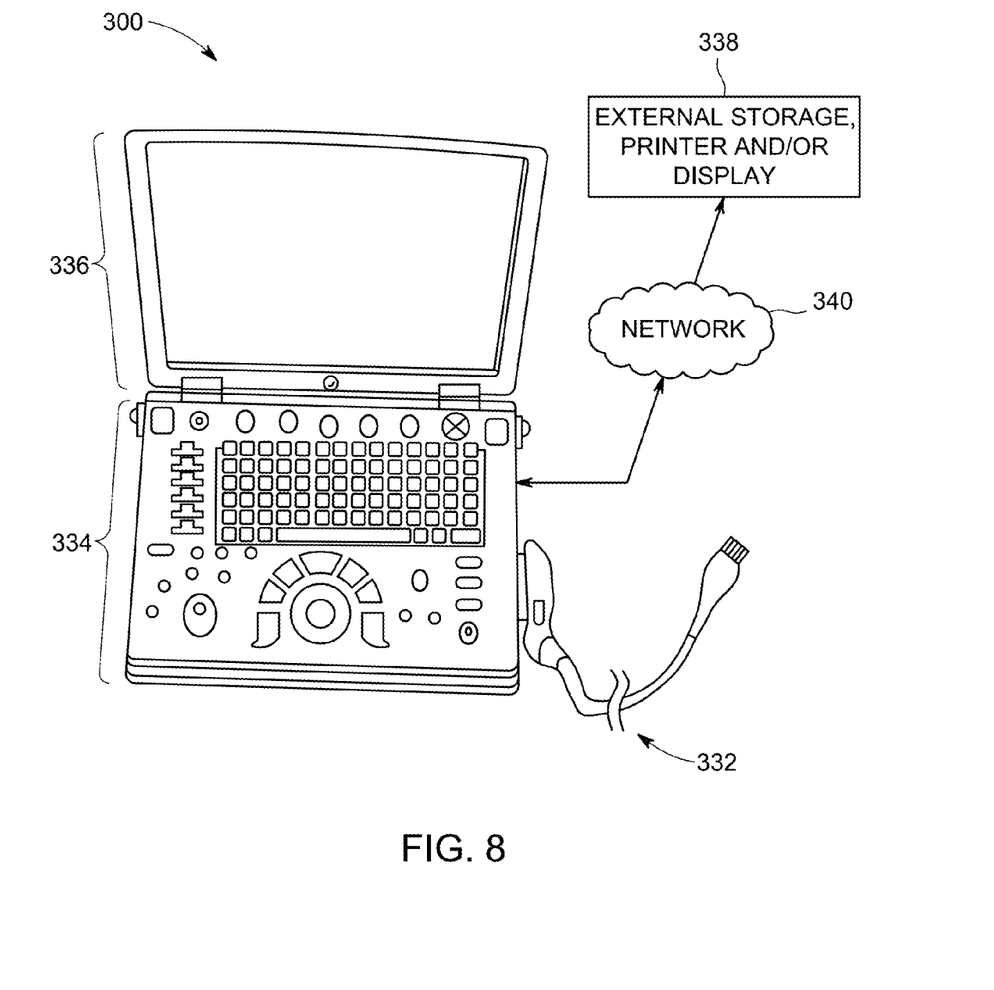
FIG. 8 is a diagram illustrating a miniaturized ultrasound system in which various embodiments may be implemented.
Figure 9:
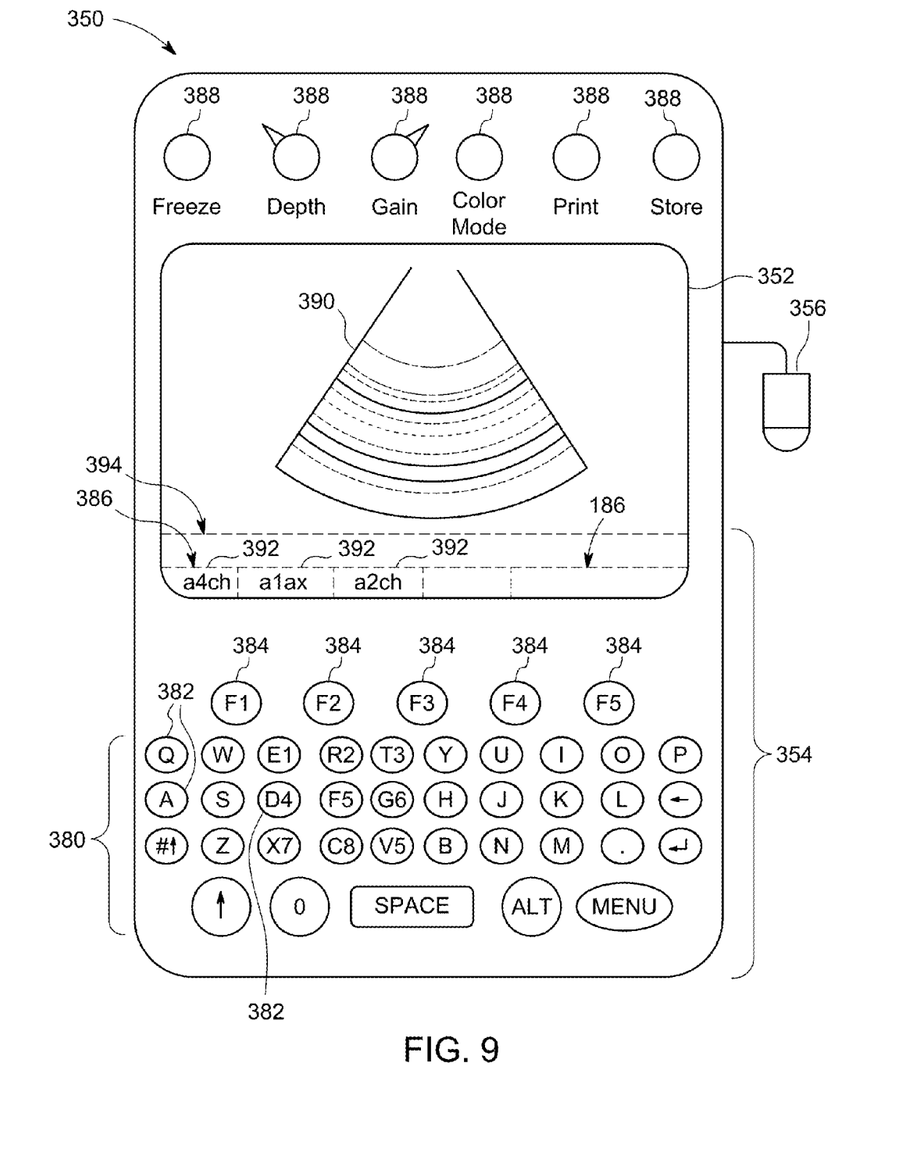
FIG. 9 is a diagram illustrating a hand carried or pocket-sized ultrasound imaging system in which various embodiments may be implemented.
Figure 10:
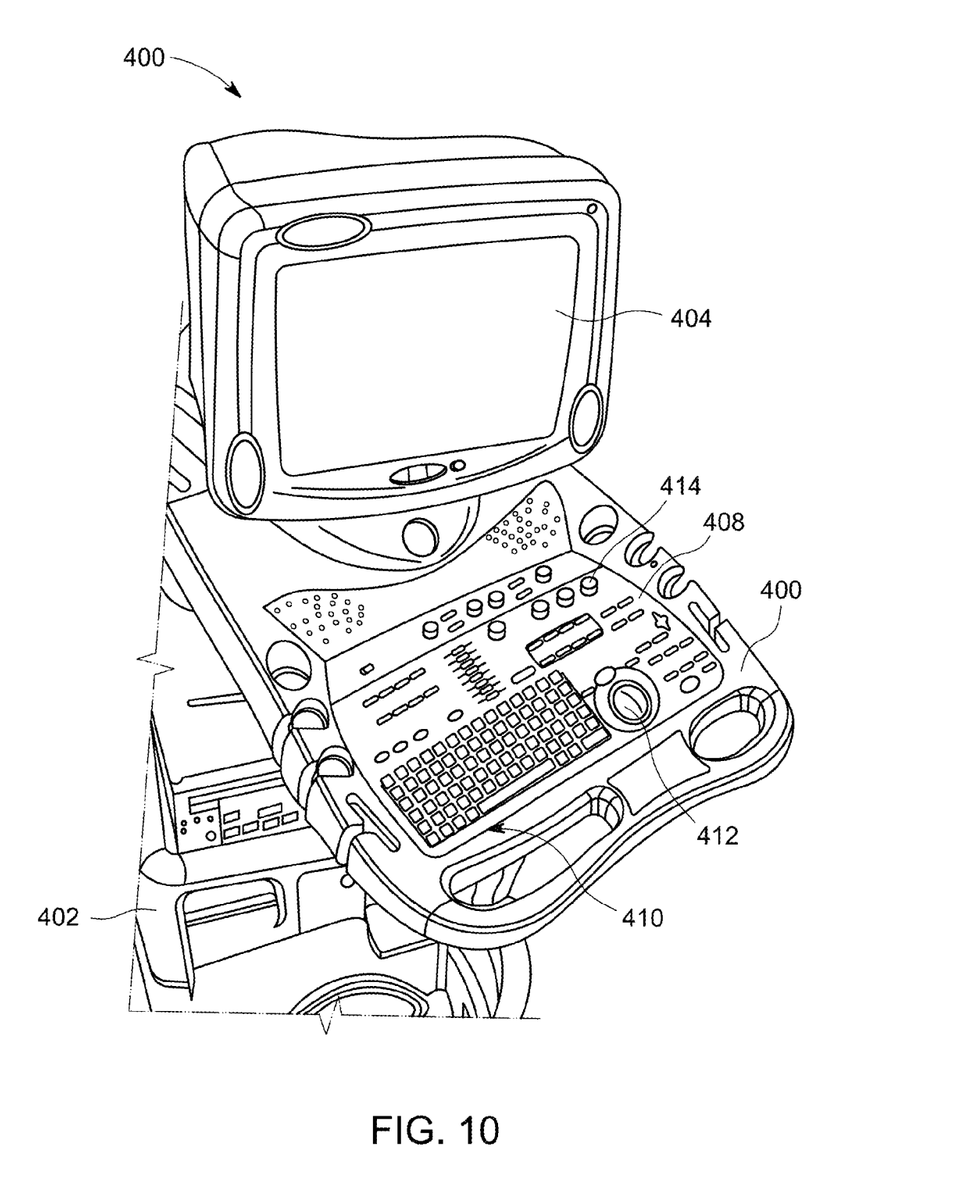
FIG. 10 is a diagram illustrating a console type ultrasound imaging system in which various embodiments may be implemented.

The system 100 of FIG. 1 may be embodied in a small-sized system, such as laptop computer or pocket sized system as well as in a larger console-type system. FIGS. 8 and 9 illustrate small-sized systems, while FIG. 10 illustrates a larger system.

FIG. 8 illustrates a 3D-capable miniaturized ultrasound system 300 having a probe 332 that may be configured to acquire 3D ultrasonic data or multi-plane ultrasonic data. For example, the probe 332 may have a 2D array of elements 104 as discussed previously with respect to the probe 106 of FIG. 1. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

FIG. 9 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, an ultrasound probe 356. The display 352 may be, for example, a 320×320 pixel color LCD display (on which a medical image 390 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 300 may provide the same scanning and processing functionality as the system 100 (shown in FIG. 1).

FIG. 10 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412, and/or multi-function controls 414 may be provided.

It should be noted that although the various embodiments may be described in connection with an ultrasound system, the methods and systems are not limited to ultrasound imaging or a particular configuration thereof. The various embodiments of ultrasound imaging may be implemented in combination with different types of imaging systems, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

It should be noted that the particular arrangement of components (e.g., the number, types, placement, or the like) of the illustrated embodiments may be modified in various alternate embodiments. In various embodiments, different numbers of a given module, system, or unit may be employed, a different type or types of a given module, system, or unit may be employed, a number of modules, systems, or units (or aspects thereof) may be combined, a given module, system, or unit may be divided into plural modules (or sub-modules), systems (or sub-systems) or units (or sub-units), a given module, system, or unit may be added, or a given module, system or unit may be omitted.

It should be noted that the various embodiments may be implemented in hardware, software or a combination thereof. The various embodiments and/or components, for example, the modules, systems, or components and controllers therein, also may be implemented as part of one or more computers or processors. The computer or processor may include a computing device, an input device, a display unit, and an interface. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor.

As used herein, the term "computer," "controller," "system", and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module", "system", or "computer."

The computer, module, system, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, system, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs, systems, or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from the scope thereof. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, paragraph (f), unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for setting parameters for image analysis of ultrasound images, the method comprising:
    obtaining ultrasound data of an object;
    generating an image of the object;
    identifying a region of interest in the image;
    mapping from the region of interest into a parameter within a predefined parameter space, wherein the mapping maps a plurality of sections in a normalized image domain to one of a scalar value or a vector value corresponding to parameters of an image analysis algorithm used to perform the image analysis;
    determining a plurality of spatially varying parameters for the image analysis of the region of interest using the mapping and prior information for one or more objects of interest, wherein the prior information comprises prior location information for the one or more objects of interest, wherein the plurality of spatially varying parameters is determined for a plurality of sections of the region of interest, and wherein at least some of the plurality of sections of the region of interest have different spatially varying parameters;
    using the plurality of spatially varying parameters for performing the image analysis of the region of interest in the image to determine a location of the one or more objects of interest.

2. The method of claim 1, further comprising using a training dataset to determine the prior information, the training dataset including comprising characteristics of the one or more objects of interest.

3. The method of claim 1, further comprising using one or more physical models of the one or more objects of interest to determine the prior information, wherein the one or more physical models define an image formation process.

4. The method of claim 1, further comprising using prior anatomical information with the prior location information as the prior information.

5. The method of claim 1, further comprising using a function that comprises the parameter in the predefined parameter space to determine the plurality of spatially varying parameters, wherein the function defines a likelihood of the presence of the one or more objects of interest in one or more of the plurality of sections of the region of interest.

6. The method of claim 5, further comprising determining a threshold for identifying the presence of the one or more objects of interest in one or more of the plurality of sections of the region of interest using the function.

7. The method of claim 1, further comprising using a function that comprises the parameter in the predefined parameter space to determine the plurality of spatially varying parameters, wherein the function defines an expected value of a standard deviation of random noise affecting the region of interest, and using the standard deviation as a spatially varying standard deviation in a probability model for the random noise in the plurality of sections of the region of interest.

8. The method of claim 1, wherein the mapping comprises performing image registration to map one coordinate system to a different coordinate system.

9. The method of claim 1, wherein the prior information further comprises prior images from one or more different anatomical features of interest.

10. A method for setting parameters for image analysis of ultrasound images, the method comprising:
    obtaining ultrasound data of an object;
    generating an image of the object;
    identifying a region of interest in the image;
    mapping from the region of interest into a parameter within a predefined parameter space, wherein the mapping maps a plurality of sections in a normalized image domain to one of a scalar value or a vector value corresponding to parameters of an image analysis algorithm used to perform the image analysis;
    determining a plurality of spatially varying parameters for the image analysis of the region of interest using the mapping and prior information for one or more objects of interest, wherein the prior information defines a relative prior frequency of an occurrence of the one or more objects of interest in one or more different locations within the region of interest; and using the plurality of spatially varying parameters for performing the image analysis of the region of interest in the image to determine a location of the one or more objects of interest.

11. The method of claim 10, further comprising using false positive information for the one or more objects of interest when determining the plurality of spatially varying parameters.

12. The method of claim 10, further comprising forming an atlas of the plurality of spatially varying parameters, the atlas comprising a plurality of sections of the region of interest, wherein at least some of the plurality of sections of the region of interest have different spatially varying parameters.

13. The method of claim 10, further comprising updating one or more of the plurality of spatially varying parameters using feedback from the image analysis.

14. The method of claim 10, wherein using the spatially varying parameters comprises using determined values for the spatially varying parameters as an input for the image analysis.

15. The method of claim 10, wherein using the spatially varying parameters comprises using determined values for the spatially varying parameters as an output for the image analysis.

16. An ultrasound system, comprising:
a probe configured to acquire ultrasound data;
a processor configured to generate image data based on the ultrasound data;
a parameter setting system configured to:
generate an image based on the image data;
identify a region of interest in the image;
generate a mapping from the region of interest into a parameter within a predefined parameter space, wherein the mapping maps a plurality of sections in a normalized image domain to one of a scalar value or a vector value corresponding to parameters of an image analysis algorithm used to perform image analysis;
determine a plurality of spatially varying parameters for the image analysis of the region of interest using the mapping and prior information for one or more objects of interest, wherein the prior information comprises prior location information for the one or more objects of interest, wherein the plurality of spatially varying parameters is determined for a plurality of sections of the region of interest, and wherein at least some of the plurality of sections of the region of interest have different spatially varying parameters; and
an image analysis system using the plurality of spatially varying parameters for performing the image analysis of the region of interest to determine a location of the one or more objects of interest.

17. The ultrasound system of claim 16, wherein the parameter setting system uses a relative prior frequency of an occurrence of the one or more objects of interest in one or more of the plurality of sections of the region of interest to determine the plurality of spatially varying parameters.

* * * * *